United States Patent [19]

Dudek

[11] Patent Number: 4,997,100

[45] Date of Patent: Mar. 5, 1991

[54] UNITARY BIOLOGICAL SPECIMEN PROCESSING APPARATUS

[76] Inventor: Peter P. Dudek, Jonstrupvej 269E, DK-3500 Värlösc, Denmark

[21] Appl. No.: 575,826

[22] Filed: Aug. 31, 1990

[51] Int. Cl.$^5$ .............................................. B65D 51/22
[52] U.S. Cl. .................................... 220/306; 220/307; 220/339
[58] Field of Search ............... 220/306, 339, 307, 324, 220/334

[56] References Cited

U.S. PATENT DOCUMENTS

| | | | |
|---|---|---|---|
| 4,127,221 | 11/1978 | Vere | 220/307 |
| 4,146,170 | 3/1979 | Medndurd | 220/306 |
| 4,257,537 | 3/1981 | Uhlig | 220/307 |
| 4,293,079 | 10/1981 | Lytle | 220/339 |
| 4,724,978 | 2/1988 | Cleevely et al. | 220/339 |

*Primary Examiner*—Joseph Man-Fu Moy

*Attorney, Agent, or Firm*—Fleit, Jacobson, Cohn, Price, Holman & Stern

[57] ABSTRACT

Unitary biological processing apparatus for processing specimens therein is described wherein a perforated receptacle member with two arc shaped abutment means and a third hook shaped abutment means is attached through a frangible hinge portion to a perforated lid member with two arc shaped detent means at the two edges of the lid member which are perpendicular to the lid member edge extending along the hinge portion, and a third detent means engageable with the hook shaped abutment means. When the lid member is swung about the hinge the arc shaped engagement means become engaged even before the lid member mates against the receptacle member and the two arc shaped engagement means provide with the third engagement means a three-point lock of the lid member onto the receptacle member.

4 Claims, 1 Drawing Sheet

FIG.1

UNITARY BIOLOGICAL SPECIMEN PROCESSING APPARATUS

BACKGROUND AND PRIOR ART

It is well known in the art that biological tissues can be sliced into thin sections on a microtome for subsequent microscopic examination by a pathologist, for example. In order to prepare the specimen for such slicing it must first be processed with several fluids to dehydrate the tissue, to clear the tissue with a suitable oil and then to infiltrate the tissue with a paraffin wax or a combination of wax and resinous material. This processing has been conveniently carried out by placing the specimen in a fluid-permeable capsule and successively submerging the capsule in the necessary fluids. The resulting processed specimen is then removed from the capsule and embedded in a block of paraffin wax for subsequent mounting in a microtome for slicing.

U.S. Pat. No. 4,220,252 describes a unitary biological specimen processing apparatus comprising an open-topped, perforated receptacle member, a cooperable perforated cover member attached to said receptable member by a frangible hinge portion, said receptacle and cover members being capable of relative movement about said hinge portion from a first position permitting placement of a specimen in said receptacle member to a second position wherein the open top of said receptacle member is closed by said cover member, and cooperable detent and abutment means on said receptacle and cover members interengageable when said receptacle and cover members are in said second position to hold said members in said second position independently of said frangible hinge portion.

Thereby is obtained an apparatus which initially has a cover member attached by a hinge portion to a base member but which can remain mated against the base member in a closed position even with the hinge portion broken.

This prior apparatus had the disadvantage that if the hinge portion was very frangible and was broken before the cover member was mated against the base member, the user of the apparatus could loose or drop the specimen because of the lost hinge function. Contamination of the specimens and loss of expensive time could thus result. If, however, the frangible hinge portion was strong enough to resist the 180 degree of the cover member turning about into the mating position with the receptacle member, there would be a risk that it would be difficult to remove the cover member from the receptacle member when processing of the specimen was finished.

There is thus a commercial need for a unitary biological processing apparatus which has a hinge portion which is so frangible that it is broken just before the cover member is mated against the receptacle member, but without the risk that the hinge function is eliminated when the hinge portion is broken.

SUMMARY OF THE INVENTION

In accordance with the present invention a unitary biological processing apparatus for processing specimens therein is provided comprising a rectangular open-topped perforated receptacle member, an cooperable perforated lid member attached to said receptacle member by a frangible hinge portion, said receptacle and lid members being capable of relative movement about said hinge portion from a first position permitting placement of a specimen in said receptacle member to a second position wherein the open top of said receptacle member is closed by said lid member and engagement means in the form of cooperable detent and abutment means on said receptacle and lid members interengageable when said receptacle and cover members are in said second position to hold said members in said second position independently of said frangible hinge portion, wherein the said cooperable detent and abutment means on said receptacle and lid members consist of at least three sets of engagement means, each in the form of cooperable detent and abutment means of which one set of engagement means is placed closely to each end of the frangible hinge portion in the side wall of the receptacle and the lid side edge of the lid member which wall and edge are perpendicular to the hinge axis of the hinge portion, the said two sets of engagement means each comprises a detent means and an abutment means of circular arc shape, the radius of which approximately corresponds to their distance from the hinge axis of the frangible hinge portion, and the arc lengths being 22–60 degrees, preferably 35 degrees.

Thereby is obtained two supplementary hinge means to the frangible hinge portion which hinge means may take over the hinge function of the frangible hinge portion before the lid member is closed onto the receptable member. This allows the frangible hinge portion to be even so frangible that it may be broken before mating said lid member against said receptable member, so that it does not need to be broken upon removing said lid member from said receptacle member.

Furthermore these two supplementary hinge means provide at least a three point connection or securing of the lid member to the receptacle member together with the engagement means of the apparatus being provided at the lid member edge and the receptacle member sidewall being placed opposite to the frangible hinge portion.

DESCRIPTION OF THE INVENTION

Figure 1:
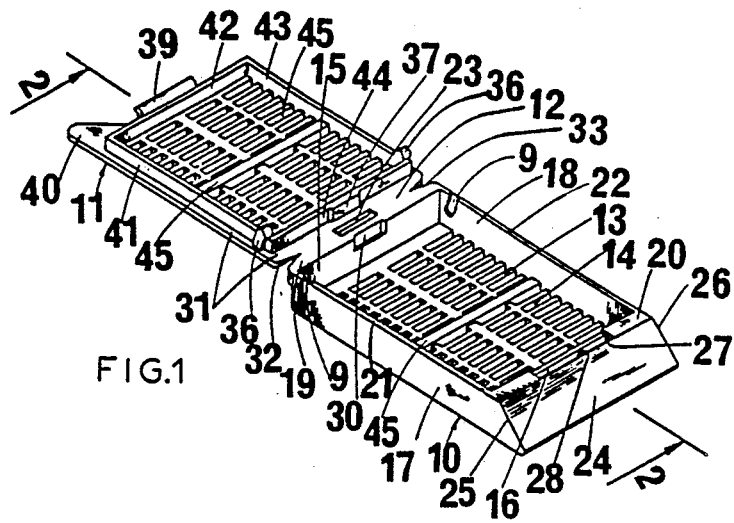
FIG. 1 is an isometric view of the apparatus of the invention in a opened or first position.
Figure 2:
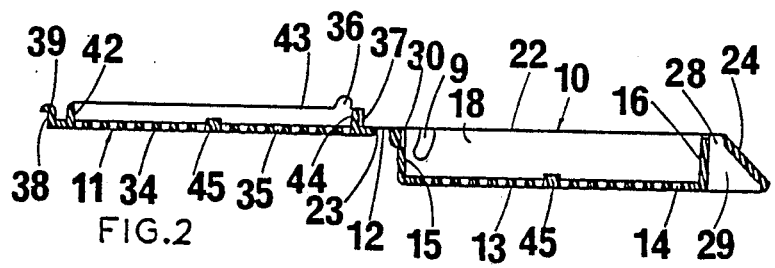
FIG. 2 is a longitudinal vertical cross-sectional view of the apparatus taken along line 2—2 of FIG. 1.

Referring to FIGS. 1 and 2, the novel apparatus of the present invention comprises a receptacle or base member 10 attached to a lid member 11 through a hinge portion 12. The open-topped box-like receptacle member 10 is formed in a generally rectangular shape with a bottom wall 13 having a plurality of rectangular perforations 14 therein, opposing parallel first and second transverse endwalls 15 and 16 and opposing parallel third and fourth longitudinal sidewalls 17 and 18 extending upward from the bottom wall 13. Endwalls 15 and 16 and sidewalls 17 and 18 have coplanar upper edge surfaces 19, 20, 21 and 22, respectively, which are normal to said endwalls and sidewalls and which form a substantially flat annular top surface for receptacle member 10.

An upper recess 30 is formed in first transverse endwall 15. This upper recess is conveniently rectangular in shape and forms a recess means. Two circular arc shaped abutment means or recesses 9 are formed in the inner side of the side walls 17, 18 and having arc lengths of 35 degrees, but these may have any value from 22–60 degrees depending of the frangibility in question aimed at for the hinge portion 12. The distance of the recesses 9 from the hinge axis of the hinge portion 12 is the same as the radius of curvature of the recesses, the hinge axis being positioned in or almost in the centres of curvature for the two recesses 9. These recesses 9 form the first and second abutment means.

Connected to and extending downwardly and outwardly from the upper edge portion 20 of the second transverse endwal 16 is a slanted wall 24, and the adjacent end portions of the longitudinal sidewalls 17 and 18 extend outwardly beyond the transverse endwall 16 to join the slanted wall 24 along slant edges 25 and 26, respectively. The upper edge portion 20 of the transverse endwall 16 is cut away as at 27 to form a transverse slot 28 which affords access to the transverse chamber 29 of generally triangular cross-section which is formed between the outer face of the transverse endwall 16 and the underside of the slanted wall 24. The portion of the slanted wall 24 at the margin of slot 28 forms a third abutment means.

The lid member 11 is formed as a flat plate 34 having an upper surface 31 which is coplanar with upper edge surface 19–22 of receptacle member transverse endwall 15. Notches 32 and 33 extending transversely inwardly from the outer edges of hinge portion 12 and slit a 23 which may be replaced by a row of perforations (not shown) will aid in rendering said hinge portion frangible. Cover member 11 preferably has a rectangular, box-like minor extension formed of walls 41, 42, 43 and 44 projecting upwardly from plate 34. The external transverse and longitudinal dimensions of this minor extension are slightly less than the corresponding internal dimensions of the open top of receptacle member 10. Flat plate 34 is formed with a plurality of rectangular perforations 35 within the walls 41 to 44. A first and second detent member is formed on the upper end of side walls 41, 43 in alignment with the respective recesses 9 on receptacle side walls 17, 18 and comprise circular arc shaped portions 36 formed in the outer side of sidewalls 41, 43 with approximately same radius of curvature and distance from the axis of the hinge portion as the recesses 9 so that the portions 36 when lid 11 is closed easily slides into the recesses 9. The lid member 11 is provided with a third detent member at the outer end edge portion of plate 34 and in alignment with the base member slot 28, said detent member being formed of a vertically extending portion 38 parallel with wall 42 and an outwardly projecting horizontal tab portion 39. Tab 39 has a transverse dimension slightly smaller than the corresponding dimension of slit 28. A lifting tab 40 is formed on the outer end of plate 34 and is coplanar therewith.

Base member 10 and cover member 11 are conveniently molded as a unitary combination structure from organoplastics, such as polyethylene, polypropylene, polystyrene, styrene-acrylonitrile copolymers, polycarbonate, formaldehyde homopolymers, copolymers of formaldehyde and trioxane, polyethylene terephthalate, polybutylene terephthalate and the like. This structure is preferably formed from formaldehyde homopolymers, copolymers of formaldehyde and trioxane, polyethylene terephthalate or polybutylene terephthalate.

Figure 3:
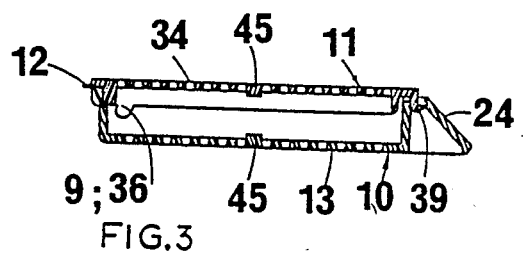
FIG. 3 is a cross-sectional view similar to that of FIG. 2 and showing the apparatus of the invention in a closed or second position.
Figure 4:
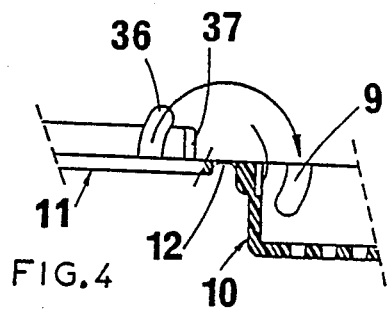
FIG. 4 is a sectional cross-sectional view similar to that of FIG. 2 but in larger scale and showing the side wall engagement principle with arc shaped engagement means.

In order to utilize the apparatus of this invention, a biological specimen is placed within the receptacle member 10 when the cover and receptacle members are in the first position shown in FIGS. 1 and 2. The lid member 11 is then rotated about the hinge portion 12 to an intermediate position to engage the circular arc shaped detent means 36 with the mating circular arc shaped recesses 9. Then the lid member 11 is further rotated to a second position to mate against the base member 10 as ahown in FIG. 3. In so doing the relief means 37 interengages upper recess 30 of transverse endwall 15 and the tab 39 of the third detent member is inserted through the transverse slot 28 and interengages the underside of the slanted wall 24. Frangible hinge portion 12 is intended to break before mating the cover member against the base member so that it is broken upon subsequently removing the cover member from the base member. If the hinge portion breaks before the above mating operation, the interengagement of the above-described detent members and abutment members will prevent undesirable separation of the lid and base members during subsequent processing steps. At the conclusion of the processing steps for the biological specimen, the lid member is conveniently removed by applying upward digital pressure on tab 40 of the cover member while applying downward digital pressure on the slanted wall 24 of the base member 10.

When that upper part of the receptacle or base member 10 sidewall 15 and that edge of the lid member 11 which are mutually connected via the frangible hinge portion 12 are provided with cooperable recess means 30 and relief means 37 as shown e.g. in FIGS. 1 and 2 is obtained that in the mated position of the lid member 11 and base member 10 no displacement of the said edge of the lid member 11 will be possible along the sidewall 15 of the receptacle 10. Thereby the form stability of the apparatus is further enforced during processing of the tissue or specimen in the apparatus or it becomes possible to provide the arc shaped engagement means 9, 36 with a cross section which is large in the plane of the arc but very small perpendicularly thereto. This reduction of the dimensions for the engagement means 9, 36 in the direction of frangible hinge portion 12 axis leaves a larger room for the specimen and its processing in the apparatus.

The slit 23 provided in the intermediate part of the frangible hinge portion 12 extending along its axis and along an intermediate part of the lid member 11 edge extending along the sidewall 15 of the base member 10 provide for a further controllable weakening of the frangible hinge portion 12 depending of the selected material for the structure, so that the likelihood will be increased that it will be broken after engagement of the arc shaped means 9, 36 and before the lid member 11 mates with the base member 10. Reinforcing ribs 45 inside the bottom wall 13 and the plate 34 enhances the stability of the three-point connection 9, 36, 28, 39 in the closed condition of the apparatus.

Another method of controlling the breaking point of the frangible hinge portion 12 is an embodiment in which the centres of curvature of the arc shaped means 9, 36 are slightly displaced relative to the axis of the hinge portion 12 in a direction perpendicular to the axis and along the surface 19, preferably in a direction towards the slanted wall 24. This displacement which may be in the order of 1-7% of the radius of curvature for the arc shaped means 9, 36 will further assist in the hinge being broken before the lid is closed completely.

What is claimed is:

1. A unitary biological specimen processing apparatus comprising a rectangular open-topped perforated receptacle member, a cooperable perforated lid member attached to said receptacle member by a frangible hinge portion, said receptacle and lid members being capable of relative movement about said hinge portion from a first position permitting placement of a specimen in said receptacle member to a second position wherein the open top of said receptacle member is closed by said lid member and engagement means in the form of cooperable detent and abutment means on said receptacle and lid members interengageable when said receptacle and cover members are in said second position to hold said members in said second position independently of said frangible hinge portion, wherein the said cooperable detent and abutment means on said receptacle and lid members consist of at least three sets of engagement means each in the form of cooperable detent and abutment means of which one set of engagement means is placed close to each end of the frangible hinge portion in the side wall of the receptacle and the lid side edge of the lid member which wall and edge are perpendicular to the hinge axis of the hinge portion, the said two sets of engagement means each comprise a detent means and an abutment means of circular arc shape, the radius of which approximately correspond to their distance from the hinge axis of the frangible hinge portion, and the arc lengths being 22-60 degrees, preferably 35 degrees.

2. Apparatus according to claim 1, wherein that upper part of the receptable sidewall and that edge of the lid member which are mutually connected via the frangible hinge portion are provided with cooperable recess means and relief means.

3. Apparatus according to claim 1, wherein a weakening means, such as a slit, a row of perforations are provided along the lid member edge next to the receptacle member preferably provided along an intermediate part of said edge, the weakening means extends parallel to the axis of the frangible hinge portion, said axis preferably passes the weakening means in its longitudinal direction.

4. Apparatus according to claim 1, wherein the centres of curvature for the arc shaped detent and abutment means are slightly displaced from the hinge axis in a direction perpendicular to the axis and along the surface 19.

* * * * *